(12) United States Patent
Kawaguchi

(10) Patent No.: US 6,413,088 B1
(45) Date of Patent: Jul. 2, 2002

(54) INSTRUMENT AND METHOD FOR REMOVING DENTAL RESTORATION

(76) Inventor: Kazuko Kawaguchi, 37, Honcho, Numazu-shi, Shizuoka-ken (JP)

(*) Notice: Subject to any disclaimer, the term of this patent is extended or adjusted under 35 U.S.C. 154(b) by 0 days.

(21) Appl. No.: 09/686,817

(22) Filed: Oct. 12, 2000

(30) Foreign Application Priority Data

Mar. 30, 2000 (JP) ........................................ 2000-094524
Jul. 18, 2000 (JP) ........................................ 2000-217731

(51) Int. Cl.$^7$ ................................................ A61C 3/16
(52) U.S. Cl. ...................................................... 433/159
(58) Field of Search ........................... 433/4, 153, 157, 433/159, 158, 161

(56) References Cited

U.S. PATENT DOCUMENTS

| | | | | |
|---|---|---|---|---|
| 1,041,601 A | * | 10/1912 | Dalton | 433/161 |
| 1,636,861 A | * | 7/1927 | Griveau | 433/159 |
| 2,944,341 A | * | 7/1960 | Lane | 433/159 |

FOREIGN PATENT DOCUMENTS

| | | |
|---|---|---|
| JP | 7-100150 | 4/1995 |
| JP | 8-56896 | 3/1996 |

OTHER PUBLICATIONS

English Language Abstract of JP 7–100150.
English Language Abstract of JP 8–56896.

* cited by examiner

Primary Examiner—Cary E. O'Connor
(74) Attorney, Agent, or Firm—Greenblum & Bernstein, P.L.C.

(57) ABSTRACT

An instrument is provided, e.g. a forceps or a pair of pliers, capable of removing a dental restoration from a tooth without destroying the dental restoration. The distal ends of a pair of jaws of the instrument each have an inner slant portion, a first outer slant portion configured to contact the boundary between the tooth and the dental restoration, and a second outer slant portion adjacent to the first outer slant portion on a side thereof remote from the boundary. When the distal ends of the jaws are disposed perpendicularly to the axis of the tooth, the inner slant portion has an inclination angle of about 20±5 degrees with respect to a horizontal plane perpendicular to the axis of the tooth. The first outer slant portion has an inclination angle of about 35±5 degrees with respect to the horizontal plane. The second outer slant portion has an inclination angle of about 1±1 degrees with respect to the horizontal plane. A method of removing a dental restoration is also provided that includes providing an instrument having a pair of pivoted handles, a pair of jaws at a distal end of each of the pair of handles, the pair of jaws including distal ends that can be wedged into a boundary between a tooth and a dental restoration from opposite sides thereof, the distal ends each having an angle whereby the tooth can be pushed downwardly and the dental restoration can be pushed upwardly. The method includes positioning the distal ends of said jaws at a boundary of a dental restoration to be removed and a tooth covered by the dental restoration, adjusting a position of the distal ends to be firmly engaged with the boundary and wedged thereinto, and repeatedly gripping the handles to apply instantaneous force to the boundary and to apply a downward pushing force on the tooth and an upward pushing force on the dental restoration to cause a joint portion of the dental restoration to disengage from the tooth.

24 Claims, 9 Drawing Sheets

INSTRUMENT AND METHOD FOR REMOVING DENTAL RESTORATION

BACKGROUND OF THE INVENTION

1. Field of the Invention

The present invention relates to an instrument for removing dental restorations, e.g. a crown restoration, a temporary crown, a post, a core, and a bridge, attached to natural teeth, artificial teeth, etc.

2. Description of Background Art

Conventional instruments for removing dental restorations are disclosed in Japanese Patent Application Unexamined Publication (KOKAI) Numbers [hereinafter referred to as "JP(A)"] 8-56960 and 7-100150.

JP(A) 8-56960 discloses a forceps- or pliers-like instrument having a pivot shaft. The instrument has a rod-shaped auxiliary member coaxially connected to the pivot shaft with a universal joint provided therebetween. To remove a dental restoration, slits are made in the dental restoration. Then, the jaws of the instrument are inserted into the slits to grip the dental restoration, and the distal end of the auxiliary member is axially tapped or pulled to thereby remove the dental restoration.

JP(A) 7-100150 discloses an instrument having a pair of levers each bent at the joint between a horizontal portion and a vertical portion in the shape of a 90-degree rotated L. Annular proximal end portions of the levers are pivotably connected together by a connecting stem. The levers have a pair of wedges projecting from the distal ends of the vertical portions so that the wedges face each other. The wedges are tapered toward each other's distal ends. The horizontal portions are connected at intermediate positions thereof by a rotating bolt so that the two bent levers can be opened or closed through threaded engagement between the rotating bolt and the horizontal portions, thereby allowing the spacing between the opposing ends of the wedges to be enlarged or reduced. To remove a dental restoration from a tooth, outer symmetric surfaces of the joint between the dental restoration and the tooth are cut to form wedge-shaped recesses with a slitter. Then, the wedges are inserted into the recesses, and the rotating bolt is rotated to reduce the spacing between the opposing ends of the wedges, thereby forcing the wedges into the recesses toward the center of the joint. By virtue of the taper formed on the wedges, when forced into the recesses, the wedges produce force acting on the tooth obliquely downward and force acting on the dental restoration obliquely upward. Consequently, the dental restoration is removed from the tooth.

However, the above-described conventional dental restoration removing instruments require that a dental restoration to be removed should be provided with slits (JP (A) 8-56960) or wedge-shaped recesses (JP (A) 7-100150) for engagement with the instrument in advance of the removal of the dental restoration. In other words, it is impossible to remove the dental restoration unless it is drilled or destroyed. Accordingly, a great deal of time is needed to remove the dental restoration, and the patient must bear the pain for an unfavorably long period of time. In addition, it takes the dentist a great deal of labor to remove the dental restoration. With the conventional dental restoration removing instruments, dental restorations once removed cannot be reused, which is unfavorable from the viewpoint of cost. Moreover, both the conventional instruments suffer from the problem that the arrangement of the instruments is completed, and the production cost is undesirably high, and further the operation is complicated.

SUMMARY OF THE INVENTION

In view of the above-described circumstances, an object of the present invention is to provide a dental restoration removing instrument free from the above-described problems with the prior art.

To attain the above-described object, the present invention provides a dental restoration removing instrument, e.g. a forceps or a pair of pliers, of the type wherein a pair of jaws at the distal end of the instrument grip an object in response to an operation of closing a pair of handles. The pair of jaws have distal ends that can be wedged into the boundary between a tooth and a dental restoration from both sides thereof. The distal end of each jaw has an angle whereby the tooth can be pushed downward and the dental restoration can be pushed upward. The instrument has an opening angle adjusting device for adjusting the opening angle between the jaws so that the distal ends of the jaws will not bite into the boundary between the tooth and the dental restoration more than a predetermined amount.

The angle is provided at the distal end of each jaw allows the jaws of the instrument to be wedged into the boundary between the tooth and the dental restoration without the need to provide slits or recesses in the dental restoration. Therefore, the instrument can be engaged with the dental restoration without destroying the latter. In addition, the dental restoration can be removed with the instrument without a possibility of undesirably pulling out the tooth together with the dental restoration, and without applying such a force that destroys the tooth or the dental restoration when the object is gripped with the instrument.

Further, because the opening angle of the instrument can be set in conformity to the tooth under treatment by adjusting the opening angle adjusting device, there is no possibility that the jaws will excessively bite into the boundary between the tooth and the dental restoration, causing the tooth or the dental restoration to be damaged.

Preferably, the distal end of each jaw has a wedge-like shape with a predetermined angle with which the distal end of each jaw is wedged into the boundary between the tooth and the dental restoration. The angle is so determined that the distal end of each jaw is disposed perpendicularly to the axis of the tooth.

By virtue of the above-described arrangement, it is possible to insert the distal ends of the jaws into the boundary between the tooth and the dental restoration while wedging the boundary by applying an upward pushing force to the dental restoration without a possibility of undesirably pulling the tooth together with the dental restoration and without applying unnecessary force to the tooth. Accordingly, the distal ends of the jaws can be readily wedged into the boundary between the tooth and the dental restoration without damage to the tooth even if the dental restoration is not provided with slits or recesses for engagement with the distal ends of the jaws.

When the instrument is gripped to remove the dental restoration, force is applied to the tooth from the outer slant portions contacting the tooth. In this case, however, the inclination angle of each outer slant portion causes the force to be applied to the tooth obliquely in a dispersed state from an upper portion at each side of the tooth toward a lower central portion thereof. Therefore, it is unlikely that the tooth, which is not very resistant to force applied vertically, will be damaged. On the other hand, strong force is applied to the dental restoration so as to push it up. Accordingly, the joint portion of the dental restoration is smoothly disengaged from the tooth, and thus the dental restoration is removed from the tooth.

Preferably, the distal end of each jaw has an inner slant portion, a first outer slant portion adapted to contact the boundary between the tooth and the dental restoration, and a second outer slant portion adjacent to the first outer slant portion on a side of the first outer slant portion remote from the boundary. The predetermined angle of the distal end of each jaw is as follows. When the distal ends of the jaws are disposed perpendicularly to the axis of the tooth, the inner slant portion has an inclination angle of about 20±5 degrees with respect to a horizontal plane perpendicular to the axis of the tooth. The first outer slant portion has an inclination angle of about 35±5 degrees with respect to the horizontal plane. The second outer slant portion has an inclination angle of about 1±1 degrees with respect to the horizontal plane.

The opening angle adjusting device may be a screw threaded into one of the pair of handles so that the distal end of the screw extending through the handle can abut on the other of the pair of handles.

With the above-described arrangement, if the extent to which the screw is threaded into the one handle is increased, the distal end of the screw abuts on the other handle at an increased angle of opening between the two handles. Consequently, the distance between the distal ends of the jaws is set large. If the extent to which the screw is threaded into the one handle is reduced, the distal end of the screw abuts on the other handle at a reduced angle of opening between the two handles. Consequently, the distance between the distal ends of the jaws is set small. Thus, the opening angle can be adjusted according to the extent to which the screw is threaded into the one handle. Accordingly, the instrument is simplified in arrangement and becomes easy to produce.

The handles may have an inclination angle of about 40 degrees with respect to the jaws when placed horizontally, whereby the distal ends of the jaws can be wedged into the boundary between a molar or the like and a dental restoration from both sides thereof.

In regard to a dental restoration removing instrument for molars, the handles are formed so as to have an inclination angle of about 35 to 40 degrees with respect to the jaws when placed horizontally, as stated above. Accordingly, it is easy to insert the instrument into the patient's mouth as far as the molar under treatment while keeping the instrument from touching any of the upper and lower front teeth and then wedge the distal ends of the jaws into the boundary between the molar under treatment and the dental restoration at right angles to the axis of the molar.

Preferably, the jaws each have a constriction formed at the distal end thereof.

In a case where the jaws of the instrument cannot be disposed at right angles to the buccal and lingual sides of the tooth under treatment when the jaws are wedged into the boundary between the tooth and the dental restoration, it may be necessary to rotate the jaws with respect to the axis of the tooth under treatment and to use the instrument in this position. In such a case, because the constriction is formed at the distal end of each jaw, there is no possibility of the jaw contacting a tooth adjacent to the tooth under treatment and causing interference with the operation. Therefore, the instrument provides excellent operability.

The dental restoration removing instrument may be arranged such that the distal ends of the jaws each have a wedge-like shape with a predetermined angle with which the distal end of each jaw is wedged into the boundary between the tooth and the dental restoration from both sides thereof, and the angle is so determined that the distal end of each jaw is disposed perpendicularly to an imaginary line connecting both sides of the boundary.

In the above-described arrangement, the distal ends of the jaws each have an inner slant portion, a first outer slant portion adapted to contact the boundary between the tooth and the dental restoration, and a second outer slant portion adjacent to the first outer slant portion on a side of the first outer slant portion remote from the boundary. The predetermined angle of the distal end of each jaw is as follows. When the distal ends of the jaws are disposed perpendicularly to the imaginary line connecting both sides of the boundary, the inner slant portion has an inclination angle of about 20±5 degrees with respect to a horizontal plane perpendicular to the axis of the tooth. The first outer slant portion has an inclination angle of about 35±5 degrees with respect to the horizontal plane. The second outer slant portion has an inclination angle of about 1±1 degrees with respect to the horizontal plane.

In another aspect of the present invention, a dental restoration removing instrument is provided, configured in the manner of a forceps or a pair of pliers, that includes a pair of pivoted handles, and a pair of jaws at a distal end of each of the pair of handles configured to grip an object in response to an operation of closing the pair of handles. The pair of jaws includes distal ends that can be wedged into a boundary between a tooth and a dental restoration from both sides thereof, the distal ends each having an angle whereby the tooth can be pushed downwardly and the dental restoration can be pushed upwardly. Additionally, the distal ends of the jaws may each have a wedge-shape with a predetermined angle with which the distal end of each jaw is wedged into the boundary between the tooth and the dental restoration, with the angle being determined such that the distal end of each jaw is disposed perpendicularly to an axis of the tooth.

According to another aspect of the present invention, the distal ends of the jaws may each have an inner slant portion, a first outer slant portion configured to contact the boundary between the tooth and the dental restoration, and a second outer slant portion adjacent to the first outer slant portion on a side of the first outer slant portion remote from the boundary. The predetermined angle of the distal end of each jaw is configured such that, when the distal ends of the jaws are disposed perpendicularly to the axis of the tooth, the inner slant portion has an inclination angle of about 20±5 degrees with respect to a horizontal plane perpendicular to the axis of the tooth, and the first outer slant portion has an inclination angle of about 35±5 degrees with respect to the horizontal plane. Furthermore, the second outer slant portion has an inclination angle of about 1±1 degrees with respect to the horizontal plane.

In a further aspect of the dental restoration removing instrument according to the present invention, an opening angle adjusting device may be provided that adjusts an opening angle between the jaws so that the distal ends of the jaws will not bite into the boundary between the tooth and the dental restoration more than a predetermined extent. Alternatively, the opening angle adjusting device may include a screw threaded into one of the pair of handles so that a distal end of the screw extending through the handle can abut on the other of the pair of handles.

In other aspects of the dental restoration removing instrument according to the present invention, the handles may have an inclination angle of about 35 to 45 degrees with respect to the jaws when placed horizontally, whereby the distal ends of the jaws can be wedged into a boundary between a molar and a dental restoration. Additionally, the jaws may each have a constriction formed at the distal end thereof. Moreover, the distal ends of the jaws may also each have a wedge-shape with a predetermined angle with which the distal end of each jaw is wedged into the boundary between the tooth and the dental restoration from both sides thereof, the angle being determined such that the distal end of each jaw is disposed perpendicularly to an imaginary line connecting both sides of the boundary.

In another aspect of the present invention, the dental restoration removing instrument according to the present invention may also include a first outer slant portion configured to contact the boundary between the tooth and the dental restoration, and a second outer slant portion adjacent to the first outer slant portion on a side of the first outer slant portion remote from the boundary. The predetermined angle of the distal end of each jaw may be configured such that, when the distal ends of the jaws are disposed perpendicularly to the imaginary line connecting both sides of the boundary, the inner slant portion has an inclination angle of about 20±5 degrees with respect to a horizontal plane perpendicular to the axis of the tooth, the first outer slant portion has an inclination angle of about 35±5 degrees with respect to the horizontal plane, and further the second outer slant portion has an inclination angle of about 1±1 degrees with respect to the horizontal plane.

According to another aspect of the present invention, a method of removing a dental restoration is provided that includes providing an instrument having a pair of pivoted handles and a pair of jaws at a distal end of each of the pair of handles, the pair of jaws including distal ends that can be wedged into a boundary between a tooth and a dental restoration from opposite sides thereof, and the distal ends each having an angle whereby the tooth can be pushed downwardly and the dental restoration can be pushed upwardly. The method also includes positioning the distal ends of the jaws at a boundary of a dental restoration to be removed and a tooth covered by the dental restoration, adjusting a position of the distal ends to be firmly engaged with the boundary and wedged thereinto, and repeatedly gripping the handles to apply instantaneous force to the boundary and to apply a downward pushing force on the tooth and an upward pushing force on the dental restoration to cause a joint portion of the dental restoration to disengage from the tooth.

In another aspect of the present invention, the method of removing a dental restoration may also include providing the distal ends of the jaws with a wedge-shape having a predetermined angle with which the distal end of each jaw is wedged into the boundary between the tooth and the dental restoration, the angle being determined such that the distal end of each jaw is disposed perpendicularly to an axis of the tooth.

In a further aspect of the present invention, the method may further include providing the distal ends of the jaws with an inner slant portion, a first outer slant portion configured to contact the boundary between the tooth and the dental restoration, and a second outer slant portion adjacent to the first outer slant portion on a side of the first outer slant portion remote from the boundary. The method further includes configuring the predetermined angle of the distal end of each jaw such that, when the distal ends of the jaws are disposed perpendicularly to the axis of the tooth, the inner slant portion has an inclination angle of about 20±5 degrees with respect to a horizontal plane perpendicular to the axis of the tooth, and the first outer slant portion has an inclination angle of about 35±5 degrees with respect to the horizontal plane, and further the second outer slant portion has an inclination angle of about 1±1 degrees with respect to the horizontal plane.

According to another aspect of the present invention, the method of removing a dental restoration may also include providing an opening angle adjusting device that adjusts an opening angle between the jaws so that the distal ends of the jaws will not bite into the boundary between the tooth and the dental restoration more than a predetermined extent. Additionally, the method may include providing the opening angle adjusting device with a screw threadable into one of the pair of handles, and adjusting the opening angle by threading the screw into the one of the pair of handles so that a distal end of the screw extending through the handle abuts on the other of the pair of handles to thereby limit the opening angle.

In further aspects of the present invention, the method of removing a dental restoration may further include providing the handles with an inclination angle of about 35 to 45 degrees with respect to the jaws when placed horizontally, whereby the distal ends of the jaws can be wedged into a boundary between a molar and a dental restoration, and providing each the jaw with a constriction formed at the distal end thereof. Additionally, the method of removing a dental restoration may further include providing the distal ends of each the jaw with a wedge-shape having a predetermined angle with which the distal end of each jaw is wedged into the boundary between the tooth and the dental restoration from both sides thereof, the angle being determined such that the distal end of each jaw is disposed perpendicularly to an imaginary line connecting both sides of the boundary.

According to a still further aspect of the present invention, the method of removing a dental restoration may further include providing the distal ends of each the jaws with an inner slant portion, a first outer slant portion configured to contact the boundary between the tooth and the dental restoration, and a second outer slant portion adjacent to the first outer slant portion on a side of the first outer slant portion remote from the boundary. The method further includes configuring the predetermined angle of the distal end of each jaw such that, when the distal ends of the jaws are disposed perpendicularly to the imaginary line connecting both sides of the boundary, the inner slant portion has an inclination angle of about 20±5 degrees with respect to a horizontal plane perpendicular to the axis of the tooth, and the first outer slant portion has an inclination angle of about 35±5 degrees with respect to the horizontal plane, and further the second outer slant portion has an inclination angle of about 1±1 degrees with respect to the horizontal plane.

BRIEF DESCRIPTION OF THE DRAWINGS

The objects and advantages of the present invention will be better understood from the following description, with reference to the accompanying drawings in which:

FIGS. 1(a), 1(b) and 1(c) show a dental restoration removing instrument for front teeth according to the present invention, in which FIG. 1(a) is a front view of the dental restoration removing instrument, FIG. 1(b) is an enlarged view showing a pair of jaws of the dental restoration removing instrument, and FIG. 1(c) is an enlarged view showing a portion of one jaw in detail;

FIGS. 5(a)–(c) are sectional side views showing the dental restoration removing instrument as wedged in the boundary between a tooth and a dental restoration attached thereto, in which: FIG. 5(a) is a sectional side view of a front tooth; FIG. 5(b) is a sectional side view of a molar; and FIG. 5(c) is an enlarged sectional side view of the molar;

FIGS. 10(a) and (b) are diagrams illustrating the dental restoration removing instrument according to the present invention in a state where the jaws thereof are rotated with respect to the axis of the tooth in actual use, in which FIG. 10(a) is a top view and FIG. 10(b) is a front view.

DETAILED DESCRIPTION OF THE PREFERRED EMBODIMENTS

Embodiments of the present invention will be described below in detail with reference to the accompanying drawings.

Figure 1A:
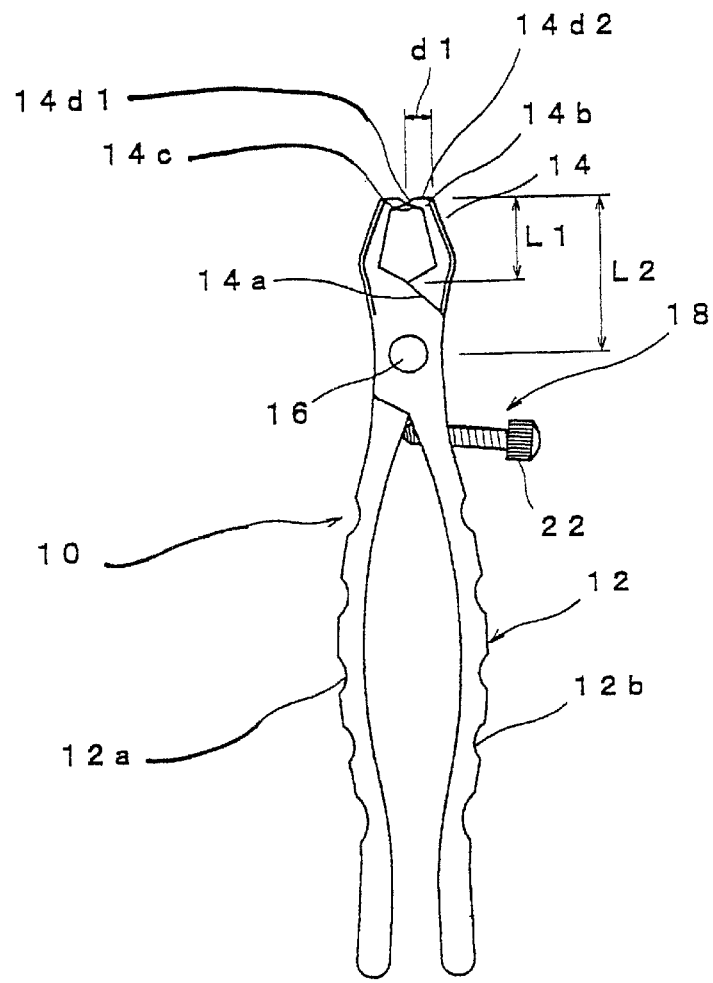
Figure 1B:
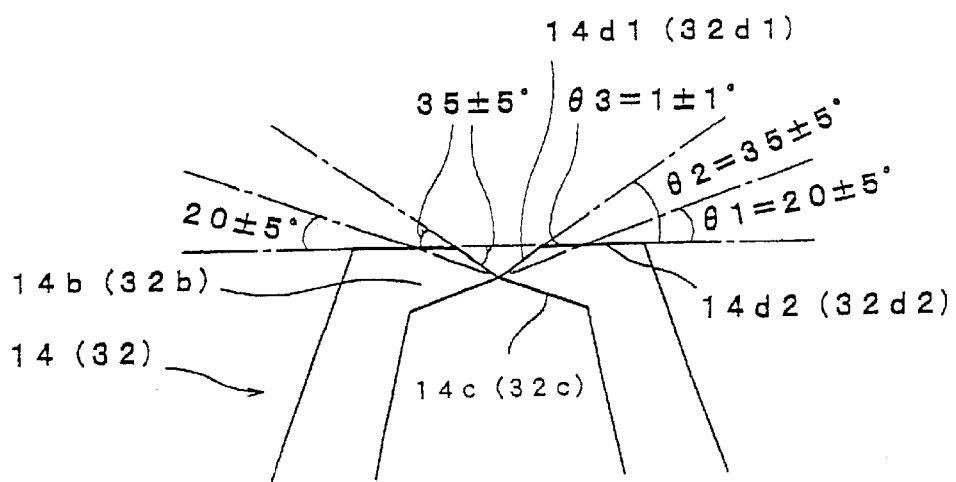
Figure 1:
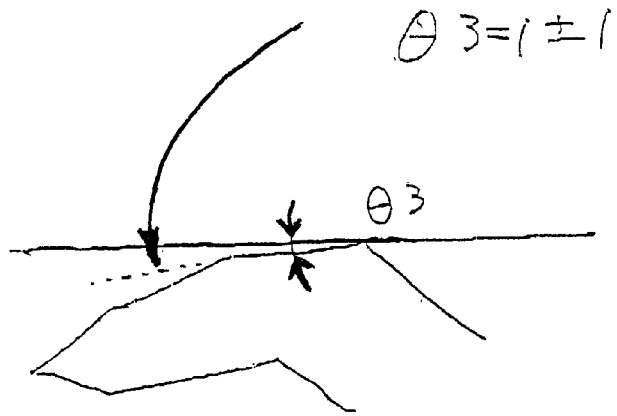
Figure 2:
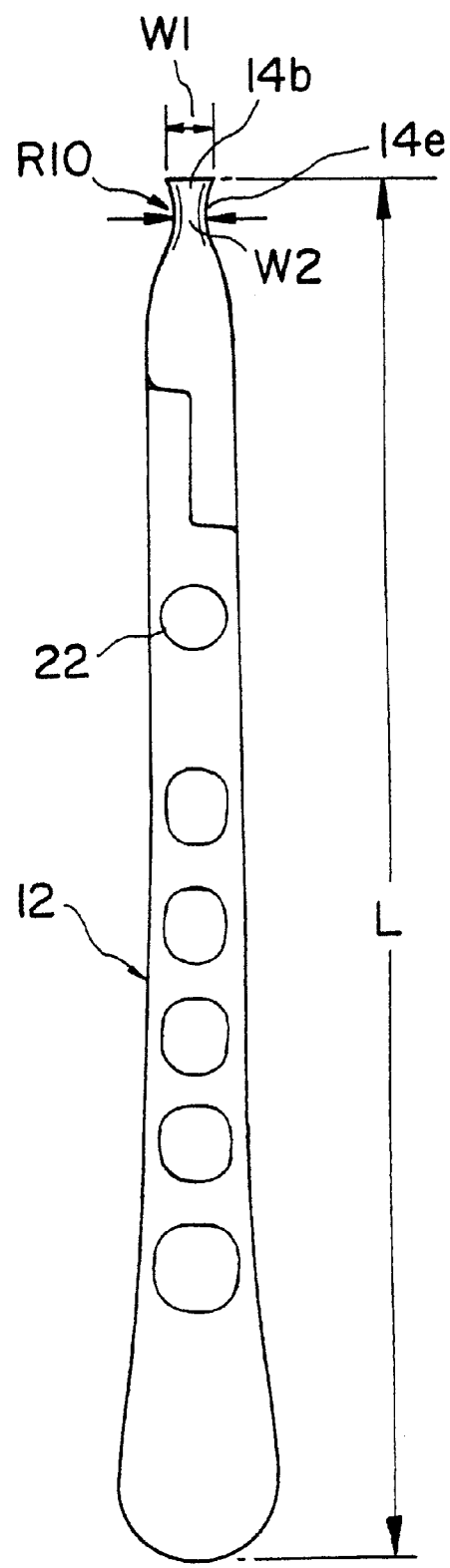
FIG. 2 is a side view of the dental restoration removing instrument for front teeth.
Figure 3:
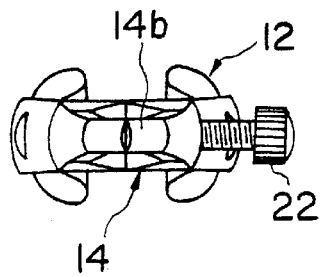
FIG. 3 is a plan view of the dental restoration removing instrument for front teeth.

First, a dental restoration removing instrument for front teeth according to the present invention will be described with reference to FIGS. 1 to 3.

A dental restoration removing instrument 10 is configured as a forceps, a pair of pliers or the like designed to grip an object with a pair of jaws 14 in response to a closing operation of a pair of handles 12. The instrument 10 may be formed of any suitable material, for example stainless steel, an example of which is SUS420J2. The weight of the instrument 10 formed of such a material is about 100 to 170 grams (but the weight will vary with the material selected). With a weight in this range, the instrument 10 provides a sense of stability and provides excellent operability. In particular, if a part of the instrument 10 that is closer to the distal end 14b (the upper end as viewed in the figures) than the center 16 of rotation is made heavier than the other part, the center of gravity comes closer to the teeth, and thus stable operability can be obtained. Accordingly, undesired movement is suppressed, and the direction of application of gripping force is stabilized. Therefore, the operation can be performed smoothly and favorably.

While the instrument 10 may have any suitable dimensions, in one embodiment of the invention, the dimensions are as follows: The overall length L is about 165.0±2.0 millimeters. The distance L1 from the proximal end 14a of each jaw 14 to the distal end 14b is about 18.0 millimeters. The distance L2 from the center of rotation 16 of the instrument 10 to the distal end 14b of each jaw 14 is about 33.0 millimeters. The length of the handles 12 is about 132.0 millimeters. However, the length of the handles 12 may be shorter than the above as long as the desired gripping can be effected. A constriction 14e is formed at the distal end 14b of each jaw 14 such that the width W2 reduces to about 4.5±2 millimeters and then enlarges with a radius of R10 to the distal end 14b. The width W1 of each distal end 14b is about 5.0±0.2 millimeters, and the length d1 of each distal end 14b is about 6.0±0.3 millimeters. The teeth generally have a width in the range of about 5.0±3 to about 10.0±3 millimeters. Therefore, the width W1 is preferably within the above range.

The distal ends 14b of the jaws 14 are in the shape of wedges capable of wedging into the boundary between a tooth and a dental restoration from both sides thereof. The distal end 14b of each jaw 14 has an inner slant portion 14c, a first outer slant portion 14d1, and a second outer slant portion 14d2. As shown in FIG. 1(b), the inner slant portion 14c has an inclination angle θ1 of about 20±5 degrees with respect to a horizontal plane perpendicular to the axis of a tooth. The first outer slant portion 14d1 has an inclination angle θ2 of about 35±5 degrees with respect to the horizontal plane perpendicular to the tooth axis. The second outer slant portion 14d2 has an inclination angle θ3 of about 1±1 degrees (note FIG. 1(c)) with respect to the horizontal plane at a side thereof closer to the first outer slant portion 14d1, which is adapted to contact a dental restoration. In other words, the second outer slant portion 14d2 is inclined slightly downward from the horizontal plane as viewed in the figure.

Due to the configuration with the above-described inclination angles, when placed to hold a tooth or a dental restoration, the distal ends 14b of the jaws 14 are disposed substantially perpendicularly to the tooth axis at the boundary between the tooth and the dental restoration. Further, the distal ends 14b of the jaws 14 can be readily inserted into the boundary between the tooth and the dental restoration by applying appropriate force to the tooth and the dental restoration. In addition, when removing the dental restoration from the tooth, it is possible to push down on the tooth optimally and to push up on the dental restoration. It should be noted that the inclination angle θ1 may be selected appropriately in the range of about 15 to about 25 degrees, and the inclination angle θ2 in the range of about 30 to about 40 degrees. As long as the inclination angles θ1 and θ2 are within these ranges, the advantageous effects of the present invention can be favorably obtained.

Figure 11:
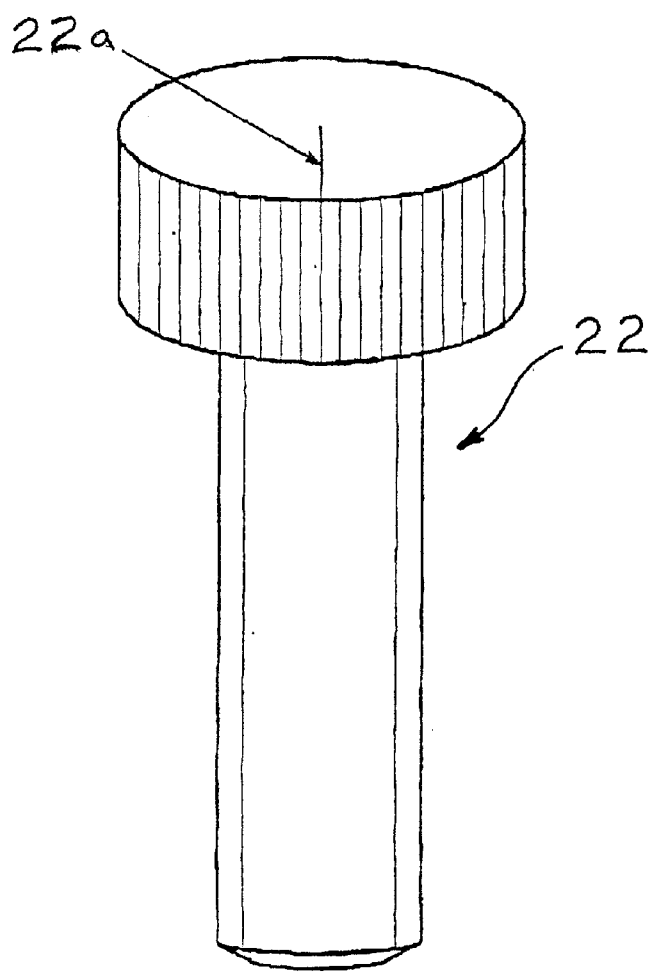
FIG. 11 is an enlarged view of an adjusting screw in accordance with the present invention.
Figure 4:
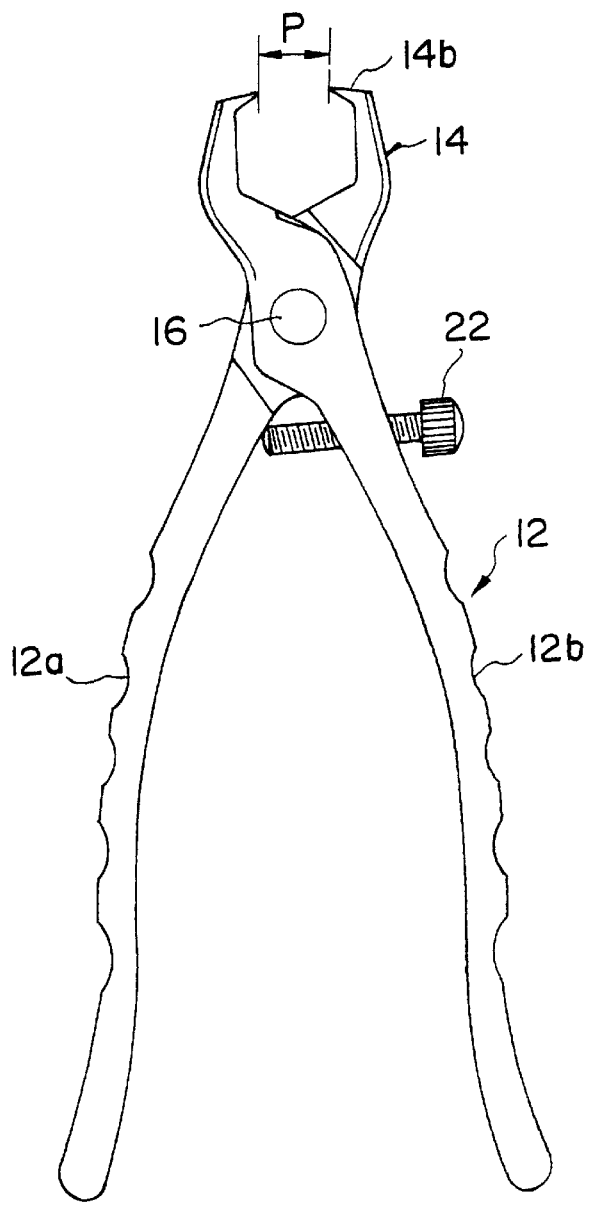
FIG. 4 is a front view showing the dental restoration removing instrument for front teeth as it is opened.

The pair of handles 12 is provided with an opening angle adjusting device 18 for adjusting the opening angle of the instrument 10. The opening angle adjusting device 18 is a screw 22 threaded into one handle 12b so that the distal end of the screw 22 extending through the handle 12b can abut on the other handle 12a. By turning the screw 22 fully once, the screw 22 moves about 1 mm in its length direction. It is desirable to provide a mark 22a, for example a laser mark, on the head of the screw 22, as shown in FIG. 11, in order to ascertain the amount of movement of the screw 22. As shown in FIG. 4, as the extent to which the screw 22 is threaded into the handle 12b increases, the opening P defined between the distal ends 14b when the jaws 14 are closed becomes larger. The opening angle adjusting device 18 is so set that the size of the opening P is within the range of 0.0 to about 20.0 millimeters.

Although a single screw 22 can be adapted for all the teeth, it is also possible to prepare a plurality of screws having different lengths so that the screws can be selectively used according to the width and diameter of teeth. For example, two different screws may be prepared: a short screw of about 20 millimeters in length for front teeth, premolars, etc.; and a long screw of about 28 millimeters in length for molars.

Next, the method of removing a dental restoration 24 will be described.

Figure 5:
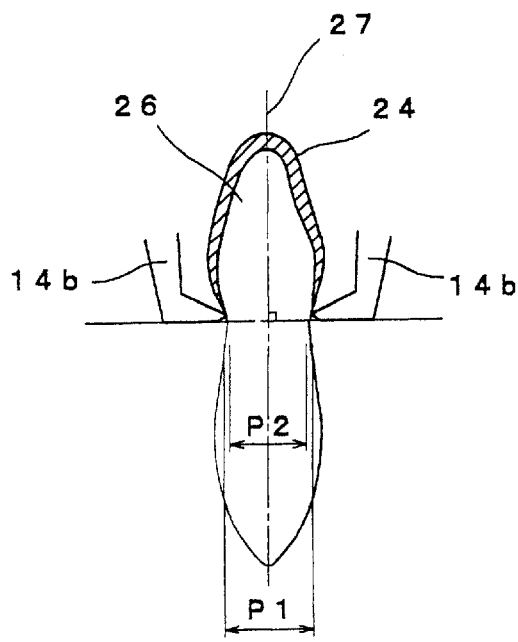
Figure 5:
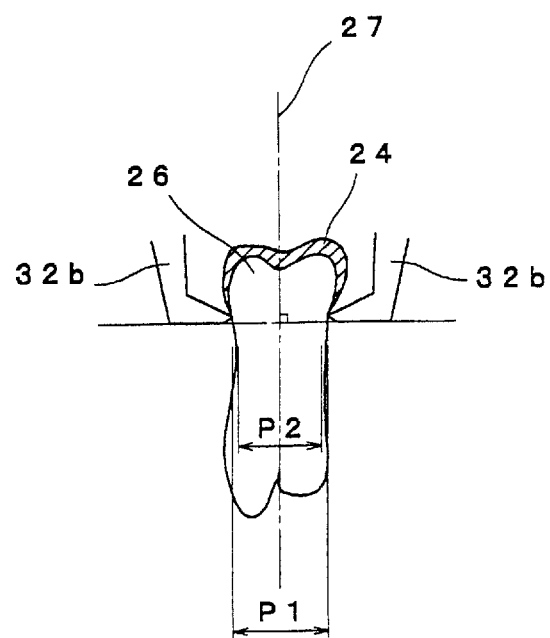
Figure 5:
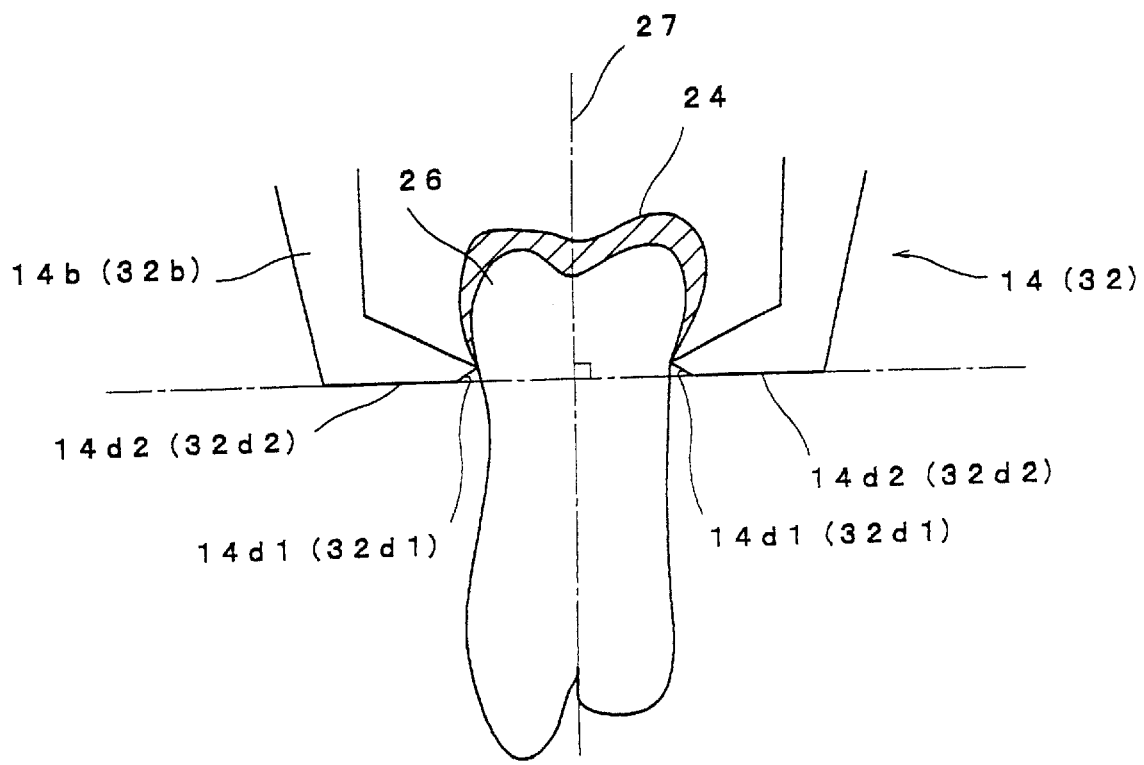

As shown in FIGS. 5(a)–(c), the distal ends 14b of the jaws 14 are wedged into the boundary between a dental restoration 24 to be removed and a tooth 26 covered with the dental restoration 24 from the buccal and lingual sides, and the positions of the distal ends 14b of the jaws 14 are adjusted so that the distal ends 14b are firmly engaged with the boundary, thereby determining a grippable position. At this time, as shown in FIG. 5(c), when the distal ends 14b (32b) of the jaws 14 (32) are placed to hold the tooth 26 or the dental restoration 24, an imaginary line connecting the edges of the distal ends 14b (32b) is disposed substantially perpendicularly to the axis 27 of the tooth 26 just below the boundary between the tooth 26 and the dental restoration 24.

Figure 10:
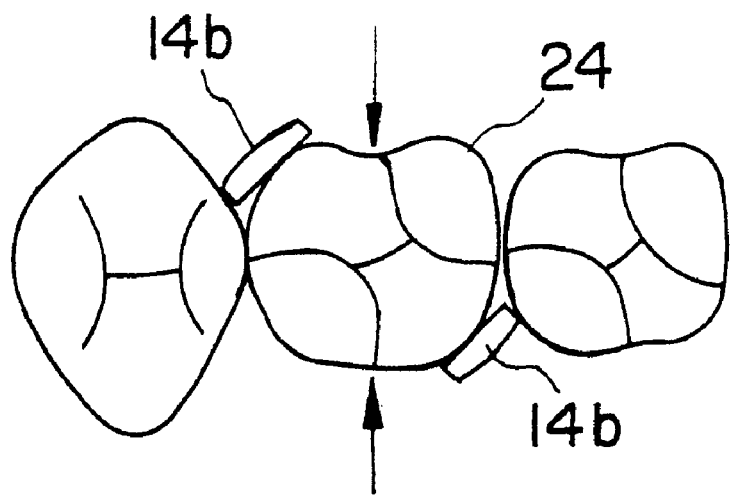
Figure 10:
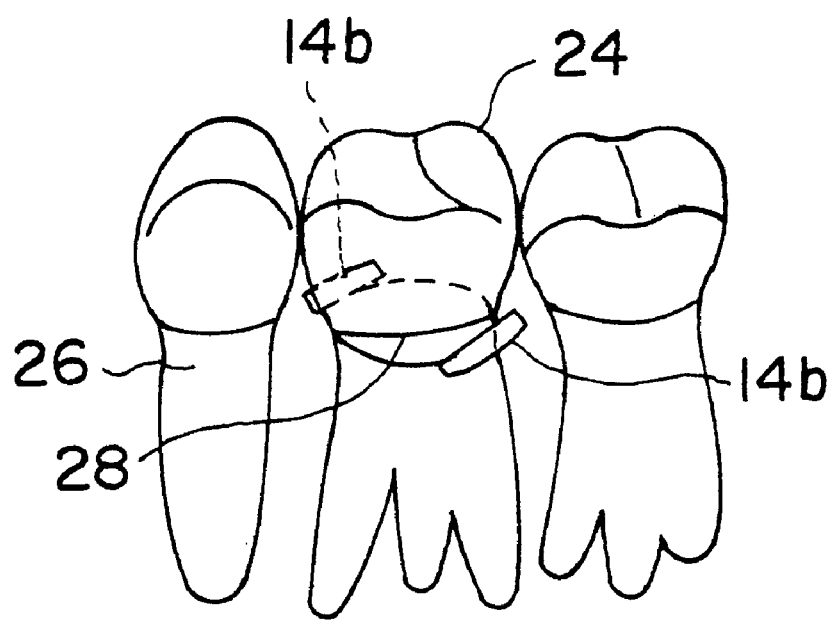

As shown in FIG. 10(a), the distal ends 14b of the jaws 14 are disposed at right angles to the buccal and lingual sides of the tooth under treatment. It should be noted that in a case where the jaws 14 of the dental restoration removing instrument cannot be placed to wedge into the boundary between the tooth under treatment and the dental restoration 24 at right angles to the buccal and lingual sides of the tooth, (e.g. in a case where the dental restoration 24 extends below the line 28 of the neck of the tooth as shown in FIG. 10(b)), the jaws 14 are rotated through about 45 degrees with respect to the axis of the tooth under treatment as shown in FIG. 10(a), and the instrument 10 is used in this position. Because the constriction 14e is formed at the distal end 14b of each jaw 14, there is no possibility of the jaw 14 contacting a tooth adjacent to the tooth under treatment and causing interference with the operation. Therefore, the instrument 10 provides excellent operability. It should be noted that the constrictions 14e of the jaws 14 have been chamfered, thereby making it possible to avoid contact between each jaw 14 and the adjacent tooth even more effectively and smoothly.

The extent to which the screw 22 is threaded into the handle 12b is adjusted so that the size of the opening P between the distal ends 14b of the jaws 14 is equal to the thickness P1 of the tooth 26 (see FIGS. 5(a) and (b)), thereby setting the opening angle of the instrument 10.

The screw 22 is loosened so that the opening P between the distal ends 14b is narrower than the thickness P1 of the tooth 26 by about 1 to 2 millimeters. That is, the jaws 14 are movable as far as the lower side of the margin of P2 (downward in the tooth axis direction), thereby determining the opening angle of the jaws 14 of the instrument 10. As a standard, in the case of a front tooth, the margin (P1-P2) is about 1–3 mm and in the case of a molar, the margin is about 2–4 mm.

As shown in FIGS. 5(a)–(c), the distal ends 14b are applied to the boundary between the tooth 26 and the dental restoration 24. Then, the handles 12a and 12b are closed to bring the distal ends 14b into engagement with the boundary.

The handles 12 of the instrument 10 are repeatedly gripped lightly to apply instantaneous force to the boundary between the tooth 26 and the dental restoration 24. By virtue of the inclination angles of the inner slant portion 14c and the first and second outer slant portions 14d1 and 14d2 of each distal end 14b, a downward pushing force acts on the tooth 26, while an upward pushing force acts on the dental restoration 24, causing the joint portion of the dental restoration 24 to disengage from the tooth 26. In this way, the dental restoration 24 is caused to slide and is thus removed from the tooth 26. The dental restoration 24 is usually removed by gripping the instrument 10 less than 5 to 6 times. In the case that the dental restoration 24 is not removed by gripping more than 5 to 6 times, it is necessary to examine the margin of the screw 22 and adjust the same.

In a case. where the position in which a dental restoration is attached to a tooth is not horizontal in terms of the positional relation between the buccal and lingual sides, the opening angle of the instrument 10 should be adjusted so that the distal ends 14b of the jaws 14 conform to the inclination angle of the joint between the dental restoration and the tooth.

Figure 6:
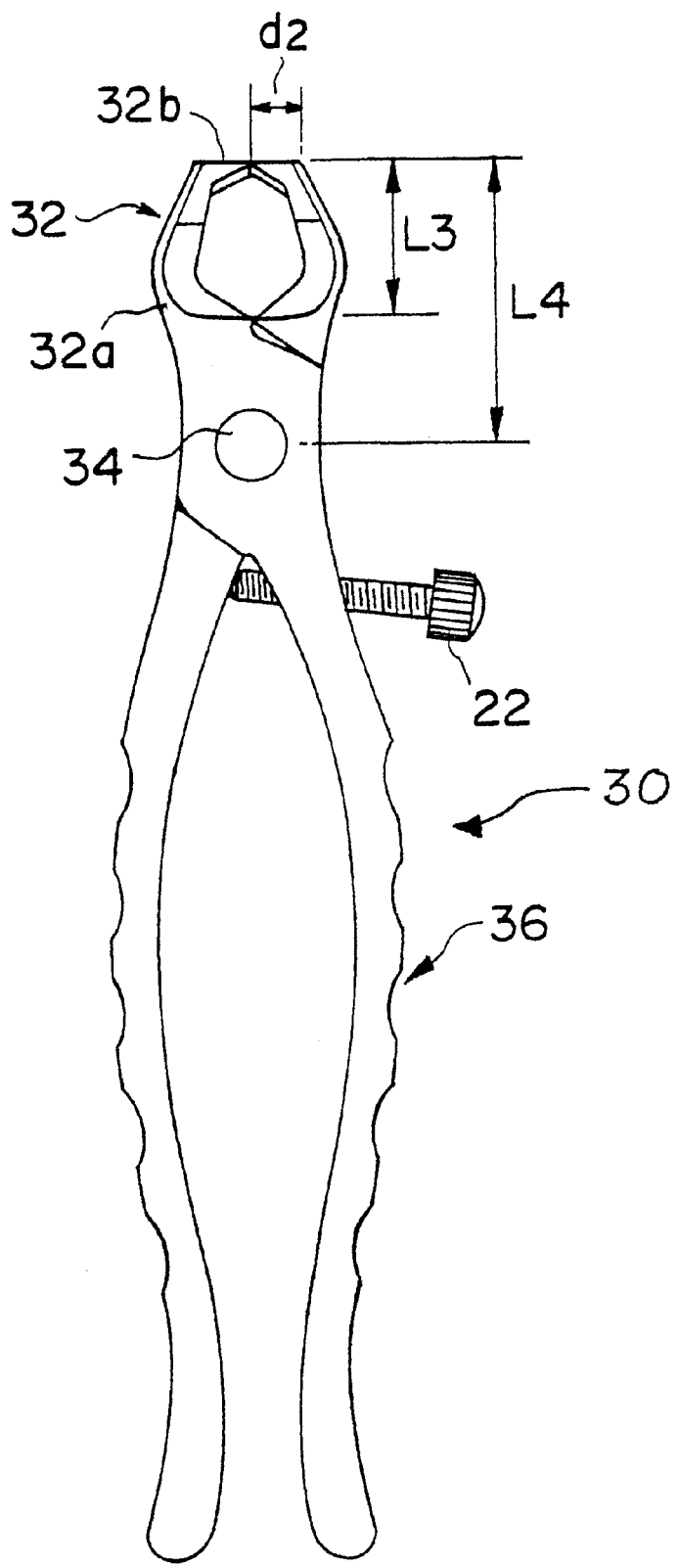
FIG. 6 is a front view of a dental restoration removing instrument for molars according to the present invention.
Figure 7:
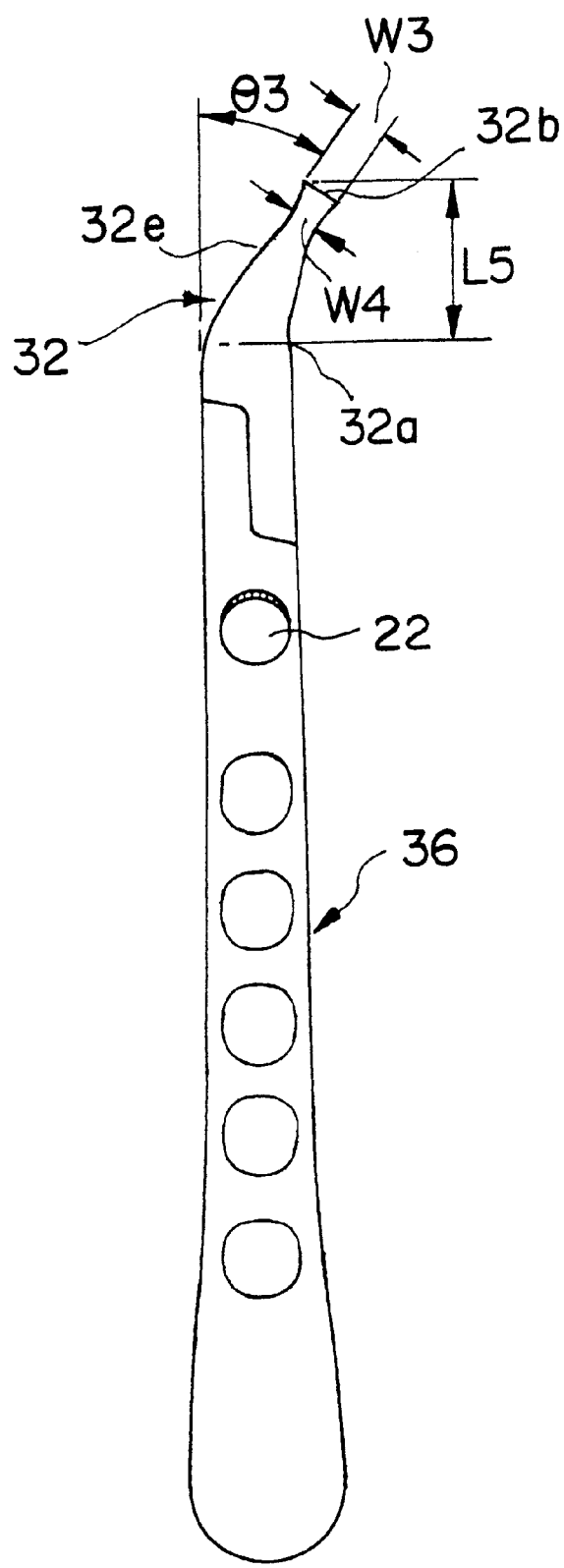
FIG. 7 is a side view of the dental restoration removing instrument for molars.
Figure 8:
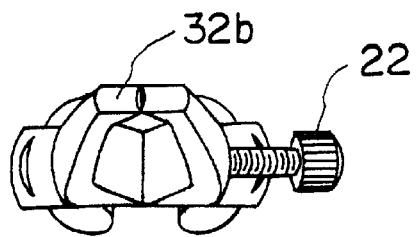
FIG. 8 is a plan view of the dental restoration removing instrument for molars.

Next, a dental restoration removing instrument 30 for molars according to the present invention will be described with reference to FIGS. 6, 7 and 8. It should be noted that the arrangement of the instrument 30 is the same as that of the above-described dental restoration removing instrument 10 for front teeth except for the arrangement described below. The method of removing a dental restoration 24 with the instrument 30 is also the same as in the case of the dental restoration removing instrument 10 for front teeth. Therefore, a description of the dental restoration removing method is omitted.

Figure 9:
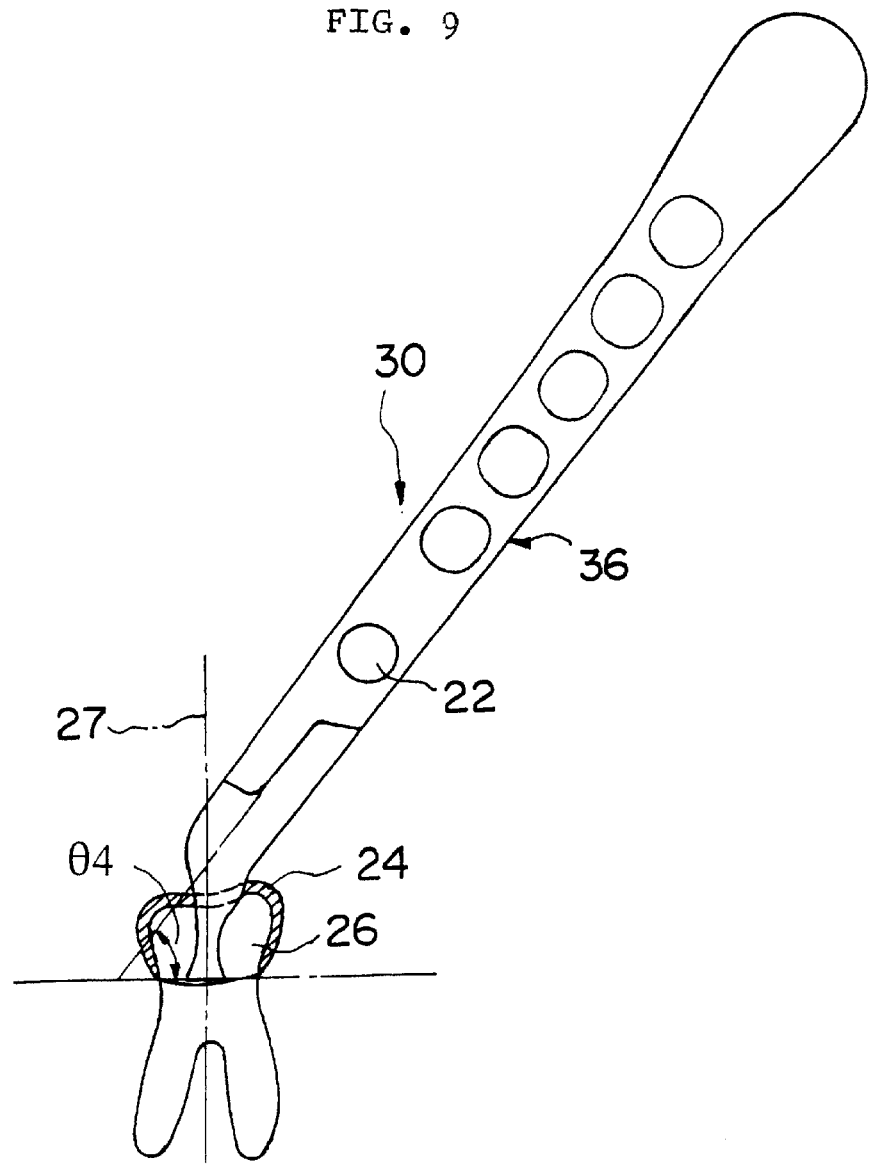
FIG. 9 is a partly-sectional side view showing the way in which the dental restoration removing instrument for molars is actually used.

While the instrument 30 may have any suitable dimensions, in another embodiment of the present invention, the dimensions are as follows: The distance L3 from the proximal end 32a of each jaw 32 to the distal end 32b thereof is about 20.0 millimeters. The distance L4 from the center of rotation 34 of the instrument 30 to the distal end 32b of each jaw 32 is about 33.0 millimeters. Each jaw 32 is narrowed at a portion near the distal end 32b so that the width W4 once reduces to about 4.0±0.2 millimeters and then enlarges with a radius of R10 to the distal end 32b. The width W3 of each distal end 32b is about 4.5±0.2 millimeters. The length d2 of each distal end 32b is about 5.0±0.3 millimeters. The jaws 32 are formed with an inclination angle θ4 (FIG. 9) of about 40 degrees with respect to the handles 36 when placed horizontally. The distance L5 in the horizontal direction from the proximal end 32a of each jaw 32 to the distal end 32b thereof is about 16.0 millimeters.

The distal ends 32b of the jaws 32 are in the shape of wedges capable of wedging into the boundary between a tooth and a dental restoration from both sides thereof. The distal end 32b of each jaw 32 has an inner slant portion 32c (note FIG. 1(b)), a first outer slant portion 32d1, and a second outer slant portion 32d2, which have respective angles similar to those of the dental restoration removing instrument 10 for front teeth. That is, as shown in FIG. 1(b), the inner slant portion 32c has an inclination angle θ1 of about 20±5 degrees with respect to a horizontal plane perpendicular to the axis of a tooth. The first outer slant portion 32d1 has an inclination angle θ2 of about 35±5 degrees with respect to the horizontal plane perpendicular to the tooth axis. The second outer slant portion 32d2 has an inclination angle θ3 of about 1±1 degrees with respect to the horizontal plane at a side thereof closer to the first outer slant portion 32d1, which is adapted to contact a dental restoration. In other words, the second outer slant portion 32d2 is inclined slightly downward from the horizontal plane as viewed in the figure.

Due to the configuration with the above-described inclination angles, when placed to hold a tooth or a dental restoration, the distal ends 32b of the jaws 32 are disposed substantially perpendicularly to the tooth axis at the boundary between the tooth and the dental restoration. Further, the distal ends 32b of the jaws 32 can be readily inserted into the boundary between the tooth and the dental restoration by applying appropriate force to the tooth and the dental restoration. In addition, when removing the dental restoration from the tooth, it is possible to push down on the tooth optimally and to push up on the dental restoration. It should be noted that the inclination angle θ1 with respect to a horizontal plane perpendicular to the tooth axis may be selected appropriately in the range of about 15 to about 25 degrees, and the inclination angle θ2 in the range of about 30 to 40 about degrees. As long as the inclination angle θ1 and θ2 are within these ranges, the advantageous effects of the present invention can be favorably obtained.

Examples of dental restorations to which the dental restoration removing instruments 10 and 30 according to the present invention are applicable to any dental restoration, examples of which include: (1) a crown restoration attached directly to a natural tooth; (2) a post buried in a natural tooth; (3) a core; (4) a bridge; and (5) a crown restoration attached to an implanted tooth. With the instrument 10 or 30, approximately 80–90% or more of such dental restorations can be removed.

Although in the foregoing embodiments the screw 22 is used as the opening angle adjusting device 18, the present invention is not necessarily limited thereto. In other words, the opening angle adjusting device 18 may be any device that can adjust and control the opening angle of a forceps, a pair of pliers, etc. to control the grip range so that the distal ends of the jaws are prevented from excessively biting into the margin of the boundary between a tooth and a dental restoration attached thereto. For example, a spring having predetermined resilient force may be interposed between the handles 12 or 36 to adjust the opening angle between the jaws.

As has been stated above, according to the present invention, the instrument can be wedged into the boundary between a tooth and a dental restoration to remove the dental restoration by virtue of the angles provided on the jaws and the provision of the opening angle adjusting device. Therefore, it is unnecessary to provide slits, recesses, etc. in the dental restoration for the purpose of removing it. Consequently, the removal of the dental restoration is completed within a shortened period of time. Accordingly, the pain inflicted on the patient is easily reduced, and the dentist's labor is saved because the dental restoration can be removed quickly. Further, a dental restoration once removed can be reused as a temporary. Accordingly, costs can be reduced.

Further, in the present invention, the distal end of each jaw has a wedge-like shape with a predetermined angle with which the distal end of each jaw is wedged into the boundary between the tooth and the dental restoration. The angle is so determined that the distal end of each jaw is disposed perpendicularly to the axis of the tooth. Consequently, it is possible to insert the distal ends of the jaws into the boundary between the tooth and the dental restoration while applying upward pushing force to the dental restoration without undesirably pulling out the tooth together with the dental restoration and without applying unnecessary force to the tooth. Accordingly, the distal ends of the jaws can be readily wedged into the boundary between the tooth and the dental restoration without damage to the tooth.

In addition, when the instrument is gripped to remove the dental restoration, force is applied to the tooth obliquely in a dispersed state from an upper portion at each side of the tooth toward a lower central portion thereof by virtue of the inclination angle of each outer slant portion. Therefore, it is unlikely that the tooth, which is not very resistant to force applied vertically, will be damaged. On the other hand, strong force is applied to the dental restoration so as to push it up. Accordingly, the joint portion of the dental restoration is smoothly disengaged from the tooth, and thus the dental restoration is removed from the tooth.

Further, in the present invention, the distal end of each jaw has an inner slant portion, a first outer slant portion adapted to contact the boundary between the tooth and the dental restoration, and a second outer slant portion adjacent to the first outer slant portion on a side of the first outer slant portion remote from the boundary. The predetermined angle of the distal end of each jaw according to a preferred embodiment is as follows. When the distal ends of the jaws are disposed perpendicularly to the axis of the tooth, the inner slant portion has an inclination angle of about 20±5 degrees with respect to a horizontal plane perpendicular to the axis of the tooth. The first outer slant portion has an inclination angle of about 35±5 degrees with respect to the horizontal plane. The second outer slant portion has an inclination angle of about 1±1 degrees with respect to the horizontal plane. With this arrangement, the above-described advantageous effect can be produced even more optimally.

In addition, the opening angle can be set by adjusting the extent to which the screw is threaded into one of the pair of handles.

Further, in the present invention, the handles are formed so as to have an inclination angle of about 35 to 45 degrees with respect to the jaws when placed horizontally. Accordingly, it is easy to insert the instrument into the patient's mouth as far as the molar under treatment while keeping the instrument from touching any of the upper and lower front teeth and then wedge the distal ends of the jaws into the boundary between the molar and the dental restoration horizontally.

Further, in the present invention, the jaws each have a constriction formed at the distal end thereof. In a case where the jaws of the dental restoration removing instrument cannot be disposed at right angles to the buccal and lingual sides of the tooth under treatment when the jaws are wedged into the boundary between the tooth and the dental restoration, it may be necessary to rotate the jaws with respect to the axis of the tooth under treatment and to use the instrument in this position. In such a case, because the constriction is formed at the distal end of each jaw, there is no possibility of the jaw contacting a tooth adjacent to the tooth under treatment and causing interference with the operation. Therefore, the instrument provides excellent operability.

Further, in the present invention, the distal ends of the jaws each have a wedge-like shape with a predetermined angle with which the distal end of each jaw is wedged into the boundary between the tooth and the dental restoration from both sides thereof, and the angle is so determined that the distal end of each jaw is disposed perpendicularly to an imaginary line connecting both sides of the boundary. Accordingly, even when the boundary between the tooth and the dental restoration is not perpendicular to the tooth axis, it is possible to insert the distal ends of the jaws into the boundary between the tooth and the dental restoration while applying upward pushing force to the dental restoration without undesirably pulling out the tooth together with the dental restoration and without applying unnecessary force to the tooth. Therefore, the distal ends of the jaws can be readily wedged into the boundary between the tooth and the dental restoration without damage to the tooth.

According to the present invention, in the above-described arrangement, the distal ends of the jaws each have an inner slant portion, a first outer slant portion adapted to contact the boundary between the tooth and the dental restoration, and a second outer slant portion adjacent to the first outer slant portion on a side of the first outer slant portion remote from the boundary. When the distal ends of the jaws are disposed perpendicularly to the imaginary line connecting both sides of the boundary, the inner slant portion has an inclination angle of about 20±5 degrees with respect to a horizontal plane perpendicular to the axis of the tooth. The first outer slant portion has an inclination angle of about 1±1 degrees with respect to the horizontal plane. With this arrangement, the above-described advantageous effect can be produced even more optimally.

Although the invention has been described herein with reference to particular means, materials and embodiments, the invention is not intended to be limited to the particulars disclosed herein; rather, the invention extends to all functionally equivalent structures, methods and uses, such as are within the scope of the appended claims.

The present disclosure relates to subject matter contained in priority Japanese Application No. 2000-94524, filed on Mar. 30, 2000, and priority Japanese Application No. 2000-217731, filed on Jul. 18, 2000.

What is claimed is:

1. A dental restoration removing instrument, configured in the manner of a forceps or a pair of pliers, comprising:
    a pair of pivoted handles;
    a pair of jaws at a distal end of each of said pair of handles configured to grip an object in response to an operation of closing said pair of handles; and
    said pair of jaws including distal ends that can be wedged into a boundary between a tooth and a dental restoration from both sides thereof, said distal ends each having an angle whereby the tooth can be pushed downwardly and the dental restoration can be pushed upwardly; and
    an opening angle adjusting device that adjusts an opening angle between said jaws so that the distal ends of said jaws will not bite into the boundary between the tooth and the dental restoration more than a predetermined extent.

2. The dental restoration removing instrument according to claim 1, wherein said distal ends of said jaws each have a wedge-shape with a predetermined angle with which the distal end of each jaw is wedged into the boundary between the tooth and the dental restoration, said angle being determined such that said distal end of each jaw is disposed perpendicularly to an axis of the tooth.

3. The dental restoration removing instrument according to claim 2, wherein said distal ends of said jaws each have an inner slant portion, a first outer slant portion configured to contact the boundary between the tooth and the dental restoration, and a second outer slant portion adjacent to the first outer slant portion on a side of said first outer slant portion remote from said boundary, wherein said predetermined angle of said distal end of each jaw is configured such that, when said distal ends of said jaws are disposed perpendicularly to the axis of the tooth, said inner slant portion has an inclination angle of about 20±5 degrees with respect to a horizontal plane perpendicular to the axis of the tooth, and said first outer slant portion has an inclination angle of about 35±5 degrees with respect to said horizontal plane, and further said second outer slant portion has an inclination angle of about 1±1 degrees with respect to said horizontal plane.

4. The dental restoration removing instrument according to claim 1, wherein said opening angle adjusting device includes a screw threaded into one of said pair of handles so that a distal end of said screw extending through said handle can abut on the other of said pair of handles.

5. The dental restoration removing instrument according to claim 1, wherein said handles have an inclination angle of about 35 to 45 degrees with respect to said jaws when placed horizontally, whereby said distal ends of said jaws can be wedged into a boundary between a molar and a dental restoration.

6. The dental restoration removing instrument according to claim 1, wherein said jaws each have a constriction formed at the distal end thereof.

7. The dental restoration removing instrument according to claim 1, wherein said distal ends of said jaws each have a wedge-shape with a predetermined angle with which the distal end of each jaw is wedged into the boundary between the tooth and the dental restoration from both sides thereof, said angle being determined such that said distal end of each jaw is disposed perpendicularly to an imaginary line connecting both sides of said boundary.

8. The dental restoration removing instrument according to claim 7, wherein said distal ends of said jaws each have an inner slant portion, a first outer slant portion configured to contact the boundary between the tooth and the dental restoration, and a second outer slant portion adjacent to the first outer slant portion on a side of the first outer slant portion remote from said boundary, wherein said predetermined angle of said distal end of each jaw is configured such that, when the distal ends of said jaws are disposed perpendicularly to the imaginary line connecting both sides of said boundary, said inner slant portion has an inclination angle of about 20±5 degrees with respect to a horizontal plane perpendicular to the axis of the tooth, and said first outer slant portion has an inclination angle of about 35±5 degrees with respect to said horizontal plane, and further said second outer slant portion has an inclination angle of about 1±1 degrees with respect to said horizontal plane.

9. The dental restoration removing instrument according to claim 1, wherein said opening angle adjusting device includes a screw threaded into a first one of said pair of pivoted handles so that a distal end of said screw extends through said first one of said pair of pivoted handles and can abut a second one of said pair of pivoted handles, wherein as the extent to which said screw is threaded into said first one of said pair of pivoted handles increases, said opening angle between said jaws when said jaws are closed becomes larger, so that said jaws may be freely opened and may be closed to a position at which said screw abuts said second one of said pair of pivoted handles, so that the distal ends of said jaws will not bite into the boundary between the tooth and the dental restoration more than a predetermined amount.

10. A method of removing a dental restoration, comprising:
    providing an instrument having a pair of pivoted handles and a pair of jaws at a distal end of each of said pair of handles, said pair of jaws including distal ends that can be wedged into a boundary between a tooth and a dental restoration from opposite sides thereof, said distal ends each having an angle whereby the tooth can be pushed downwardly and the dental restoration can be pushed upwardly;
    positioning said distal ends of said jaws at a boundary of a dental restoration to be removed and a tooth covered by the dental restoration;
    adjusting a position of said distal ends to be firmly engaged with the boundary and wedged thereinto;
    repeatedly gripping said handles to apply instantaneous force to the boundary and to apply a downward pushing force on the tooth and an upward pushing force on the dental restoration to cause a joint portion of the dental restoration to disengage from the tooth; and providing an opening angle adjusting device that adjusts an opening angle between said jaws so that the distal ends of said jaws will not bite into the boundary between the tooth and the dental restoration more than a predetermined extent.

11. The method of removing a dental restoration according to claim 10, further comprising providing said distal ends of said jaws with a wedge-shape having a predetermined angle with which the distal end of each jaw is wedged into the boundary between the tooth and the dental restoration, said angle being determined such that said distal end of each jaw is disposed perpendicularly to an axis of the tooth.

12. The method of removing a dental restoration according to claim 11, further comprising providing said distal ends of said jaws with an inner slant portion, a first outer slant portion configured to contact the boundary between the tooth and the dental restoration, and a second outer slant portion adjacent to the first outer slant portion on a side of said first outer slant portion remote from said boundary, and configuring said predetermined angle of said distal end of each jaw such that, when said distal ends of said jaws are disposed perpendicularly to the axis of the tooth, said inner slant portion has an inclination angle of about 20±5 degrees with respect to a horizontal plane perpendicular to the axis of the tooth, and said first outer slant portion has an inclination angle of about 35±5 degrees with respect to said horizontal plane, and farther said second outer slant portion has an inclination angle of about 1±1 degrees with respect to said horizontal plane.

13. The method of removing a dental restoration according to claim 10, further comprising providing said opening angle adjusting device with a screw threadable into one of said pair of handles, and adjusting the opening angle by threading the screw into said one of said pair of handles so that a distal end of said screw extending through said handle abuts on the other of said pair of handles to thereby limit the opening angle.

14. The method of removing a dental restoration according to claim 10, further comprising providing said handles with an inclination angle of about 35 to 45 degrees with respect to said jaws when placed horizontally, whereby said distal ends of said jaws can be wedged into a boundary between a molar and a dental restoration.

15. The method of removing a dental restoration according to claim 10, further comprising providing each said jaw with a constriction formed at the distal end thereof.

16. The method of removing a dental restoration according to claim 10, further comprising providing said distal ends of each said jaw with a wedge-shape having a predetermined angle with which the distal end of each jaw is wedged into the boundary between the tooth and the dental restoration from both sides thereof, said angle being determined such that said distal end of each jaw is disposed perpendicularly to an imaginary line connecting both sides of said boundary.

17. The method of removing a dental restoration according to claim 16, further comprising providing said distal ends of each said jaws with an inner slant portion, a first outer slant portion configured to contact the boundary between the tooth and the dental restoration, and a second outer slant portion adjacent to the first outer slant portion on a side of the first outer slant portion remote from said boundary, and configuring said predetermined angle of said distal end of each jaw such that, when the distal ends of said jaws are disposed perpendicularly to the imaginary line connecting both sides of said boundary, said inner slant portion has an inclination angle of about 20±5 degrees with respect to a horizontal plane perpendicular to the axis of the tooth, and said first outer slant portion has an inclination angle of about 35±5 degrees with respect to said horizontal plane, and further said second outer slant portion has an inclination angle of about 1±1 degrees with respect to said horizontal plane.

18. The method of removing a dental restoration according to claim 10, wherein said opening angle adjusting device includes a screw threaded into a first one of said pair of pivoted handles so that a distal end of said screw extends through said first one of said pair of pivoted handles and can abut a second one of said pair of pivoted handles, and said method further comprises threading said screw into said first one of said pair of pivoted handles so that said opening angle between said jaws when said jaws are closed becomes larger, and so that said jaws may be freely opened and may be closed to a position at which said screw abuts said second one of said pair of pivoted handles, thereby preventing the distal ends of said jaws from biting into the boundary between the tooth and the dental restoration more than a predetermined amount.

19. A dental restoration removing instrument, configured in the manner of a forceps or a pair of pliers, comprising:
 a pair of pivoted handles;
 a pair of jaws at a distal end of each of said pair of handles configured to grip an object in response to an operation of closing said pair of handles;
 said pair of jaws including distal ends that can be wedged into a boundary between a tooth and a dental restoration from both sides thereof, said distal ends each having a predetermined angle configured to push the tooth downwardly and to push the dental restoration upwardly; and
 wherein each said predetermined angle of said distal ends of said jaws comprises an inner slant portion, a first outer slant portion configured to contact the boundary between the tooth and the dental restoration, and a second outer slant portion adjacent to the first outer slant portion on a side of said first outer slant portion remote from said boundary, wherein said predetermined angle of said distal end of each jaw is configured such that, when said distal ends of said jaws are disposed perpendicularly to the axis of the tooth, said inner slant portion has an inclination angle of about 20±5 degrees with respect to a horizontal plane perpendicular to the axis of the tooth, and said first outer slant portion has an inclination angle of about 35±5 degrees with respect to said horizontal plane, and further said second outer slant portion has an inclination angle of about 1±1 degrees with respect to said horizontal plane.

20. A dental restoration removing instrument, configured in the manner of a forceps or a pair of pliers, comprising:
 a pair of pivoted handles;
 a pair of jaws at a distal end of each of said pair of handles configured to grip an object in response to an operation of closing said pair of handles;
 said pair of jaws including distal ends that can be wedged into a boundary between a tooth and a dental restoration from both sides thereof, said distal ends each having an angle configured to push the tooth downwardly and to push the dental restoration upwardly; and
 an opening angle adjusting device that adjusts an opening angle between said jaws so that the distal ends of said jaws will not bite into the boundary between the tooth and the dental restoration more than a predetermined amount; and wherein said opening angle adjusting device includes a screw threaded into one of said pair of handles so that a distal end of said screw extending through said handle can abut on the other of said pair of handles.

21. A dental restoration removing instrument, configured in the manner of a forceps or a pair of pliers, comprising:

a pair of pivoted handles;

a pair of jaws at a distal end of each of said pair of handles configured to grip an object in response to an operation of closing said pair of handles;

said pair of jaws including distal ends that can be wedged into a boundary between a tooth and a dental restoration from both sides thereof, said distal ends each having a predetermined angle configured to push the tooth downwardly and to push the dental restoration upwardly; and wherein each said predetermined angle of said distal ends of said jaws comprises an inner slant portion, a first outer slant portion configured to contact the boundary between the tooth and the dental restoration, and a second outer slant portion adjacent to the first outer slant portion on a side of the first outer slant portion remote from said boundary, wherein said predetermined angle of said distal end of each jaw is configured such that, when the distal ends of said jaws are disposed perpendicularly to the imaginary line connecting both sides of said boundary, said inner slant portion has an inclination angle of about 20±5 degrees with respect to a horizontal plane perpendicular to the axis of the tooth, and said first outer slant portion has an inclination angle of about 35±5 degrees with respect to said horizontal plane, and further said second outer slant portion has an inclination angle of about 1±1 degrees with respect to said horizontal plane.

22. A method of removing a dental restoration, comprising:

providing an instrument having a pair of pivoted handles and a pair of jaws at a distal end of each of said pair of handles, said pair of jaws including distal ends that can be wedged into a boundary between a tooth and a dental restoration from opposite sides thereof, said distal ends each having a predetermined angle configured to push the tooth downwardly and to push the dental restoration upwardly;

positioning said distal ends of said jaws at a boundary of a dental restoration to be removed and a tooth covered by the dental restoration;

adjusting a position of said distal ends to be firmly engaged with the boundary and wedged thereinto;

repeatedly gripping said handles to apply instantaneous force to the boundary and to apply a downward pushing force on the tooth and an upward pushing force on the dental restoration to cause a joint portion of the dental restoration to disengage from the tooth; and providing each said predetermined angle of said distal ends of said jaws with an inner slant portion, a first outer slant portion configured to contact the boundary between the tooth and the dental restoration, and a second outer slant portion adjacent to the first outer slant portion on a side of said first outer slant portion remote from said boundary, and configuring said predetermined angle of said distal end of each jaw such that, when said distal ends of said jaws are disposed perpendicularly to the axis of the tooth, said inner slant portion has an inclination angle of about 20±5 degrees with respect to a horizontal plane perpendicular to the axis of the tooth, and said first outer slant portion has an inclination angle of about 35±5 degrees with respect to said horizontal plane, and further said second outer slant portion has an inclination angle of about 1±1 degrees with respect to said horizontal plane.

23. A method of removing a dental restoration, comprising:

providing an instrument having a pair of pivoted handles and a pair of jaws at a distal end of each of said pair of handles, said pair of jaws including distal ends that can be wedged into a boundary between a tooth and a dental restoration from opposite sides thereof, said distal ends each having an angle configured to push the tooth downwardly and to push the dental restoration upwardly;

positioning said distal ends of said jaws at a boundary of a dental restoration to be removed and a tooth covered by the dental restoration;

adjusting a position of said distal ends to be firmly engaged with the boundary and wedged thereinto;

repeatedly gripping said handles to apply instantaneous force to the boundary and to apply a downward pushing force on the tooth and an upward pushing force on the dental restoration to cause a joint portion of the dental restoration to disengage from the tooth; and providing said opening angle adjusting device with a screw threadable into one of said pair of handles, and adjusting the opening angle by threading the screw into said one of said pair of handles so that a distal end of said screw extending through said handle abuts on the other of said pair of handles to thereby limit the opening angle.

24. A method of removing a dental restoration, comprising:

providing an instrument having a pair of pivoted handles and a pair of jaws at a distal end of each of said pair of handles, said pair of jaws including distal ends that can be wedged into a boundary between a tooth and a dental restoration from opposite sides thereof, said distal ends each having a predetermined angle configured to push the tooth downwardly and to push the dental restoration upwardly;

positioning said distal ends of said jaws at a boundary of a dental restoration to be removed and a tooth covered by the dental restoration;

adjusting a position of said distal ends to be firmly engaged with the boundary and wedged thereinto;

repeatedly gripping said handles to apply instantaneous force to the boundary and to apply a downward pushing force on the tooth and an upward pushing force on the dental restoration to cause a joint portion of the dental restoration to disengage from the tooth; and providing each said predetermined angle of said distal ends of said jaws with an inner slant portion, a first outer slant portion configured to contact the boundary between the tooth and the dental restoration, and a second outer slant portion adjacent to the first outer slant portion on a side of the first outer slant portion remote from said boundary, and configuring said predetermined angle of said distal end of each jaw such that, when the distal ends of said jaws are disposed perpendicularly to the imaginary line connecting both sides of said boundary, said inner slant portion has an inclination angle of about 20±5 degrees with respect to a horizontal plane perpendicular to the axis of the tooth, and said first outer slant portion has an inclination angle of about 35±5 degrees with respect to said horizontal plane, and further said second outer slant portion has an inclination angle of about 1±1 degrees with respect to said horizontal plane.

* * * * *

UNITED STATES PATENT AND TRADEMARK OFFICE
CERTIFICATE OF CORRECTION

PATENT NO. : 6,413,088 B1
DATED : July 2, 2002
INVENTOR(S) : K. Kawaguchi

It is certified that error appears in the above-identified patent and that said Letters Patent is hereby corrected as shown below:

Column 15,
Line 30, "farther" should be -- further --.

Signed and Sealed this

Twenty-fifth Day of February, 2003

JAMES E. ROGAN
*Director of the United States Patent and Trademark Office*